(12) United States Patent
Kuang et al.

(10) Patent No.: US 11,517,706 B2
(45) Date of Patent: Dec. 6, 2022

(54) FUNCTIONAL ELECTRICAL STIMULATION DEVICE FOR REDUCING PREOPERATIVE AND PRENATAL ANXIETY AND METHOD FOR USING SAME

(71) Applicant: SOOCHOW UNIVERSITY, Suzhou (CN)

(72) Inventors: Shaolong Kuang, Suzhou (CN); Xiao Cheng, Suzhou (CN); Yinfang Fang, Suzhou (CN); Yucun Tang, Suzhou (CN); Fangxia Li, Suzhou (CN); Shuai Wu, Suzhou (CN); Shumei Yu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 596 days.

(21) Appl. No.: 16/496,416

(22) PCT Filed: Dec. 18, 2017

(86) PCT No.: PCT/CN2017/116829
§ 371 (c)(1),
(2) Date: Sep. 21, 2019

(87) PCT Pub. No.: WO2019/113988
PCT Pub. Date: Jun. 20, 2019

(65) Prior Publication Data
US 2020/0016364 A1  Jan. 16, 2020

(30) Foreign Application Priority Data
Dec. 14, 2017  (CN) .......................... 201711339695.6

(51) Int. Cl.
*A61M 21/02* (2006.01)
*A61N 1/36* (2006.01)
(Continued)

(52) U.S. Cl.
CPC ......... *A61M 21/02* (2013.01); *A61N 1/36025* (2013.01); *A61N 1/36034* (2017.08);
(Continued)

(58) Field of Classification Search
CPC .......... A61M 21/02; A61M 2021/0027; A61M 2021/0072; A61M 2205/3584;
(Continued)

(56) References Cited

U.S. PATENT DOCUMENTS

2008/0051852 A1* 2/2008 Dietrich ............... A61H 39/002
607/45
2008/0146958 A1* 6/2008 Guillory ............. A61B 5/4094
600/544
(Continued)

FOREIGN PATENT DOCUMENTS

CN   201524339 U   7/2010
CN   103920235 A   7/2014
(Continued)

OTHER PUBLICATIONS

EnglishTranslation of CN10392035, Jul. 16, 2014, Tang Bo et al. (see attached) (Year: 2014).*
(Continued)

*Primary Examiner* — Sunita Reddy
(74) *Attorney, Agent, or Firm* — SZDC Law P.C.

(57) ABSTRACT

The invention discloses a functional electrical stimulation device including a headset, an electrical stimulation patch, an LED display screen, a circuit board, a rechargeable battery and a wireless terminal, and a method for using same. Two headphone bodies are symmetrically disposed on the headset, the circuit board and rechargeable battery are respectively mounted on the headphone bodies, and a music control button and an electrical stimulation mode and time control button are mounted on the two headphone bodies (Continued)

respectively. Two electrical stimulation patches are mounted on a middle portion of the headset, two LED display screens are respectively mounted on the two electrical stimulation patches. An audio decoder chip, a button control module, a power switch, an electrical stimulation generation module, a wireless communications module and a charging port are disposed on the circuit board, and the wireless terminal is independently disposed and in wireless communication with the circuit board.

3 Claims, 2 Drawing Sheets

(51) Int. Cl.
    *G06F 3/16*         (2006.01)
    *H04R 1/10*         (2006.01)
    *H04W 76/10*      (2018.01)
    *A61M 21/00*      (2006.01)

(52) U.S. Cl.
    CPC .......... *G06F 3/165* (2013.01); *H04R 1/1008* (2013.01); *H04R 1/1025* (2013.01); *H04R 1/1041* (2013.01); *A61M 2021/0027* (2013.01); *A61M 2021/0072* (2013.01); *A61M 2205/3584* (2013.01); *A61M 2205/587* (2013.01); *A61M 2205/8206* (2013.01); *H04R 2420/07* (2013.01); *H04W 76/10* (2018.02)

(58) Field of Classification Search
    CPC .... A61M 2205/587; A61M 2205/8206; A61M 2021/0044; A61M 2205/3561; A61M 2205/3592; A61M 2205/505; A61N 1/36025; A61N 1/36034; A61N 1/36021; A61N 1/36014; G06F 3/165; G06F 3/167; H04R 1/1008; H04R 1/1025; H04R 1/1041; H04R 2420/07; H04W 76/10
    USPC ...................................... 600/26–28
See application file for complete search history.

(56) References Cited

U.S. PATENT DOCUMENTS

| | | | |
|---|---|---|---|
| 2010/0036445 A1* | 2/2010 | Sakai | A61N 1/0551 607/116 |
| 2011/0160811 A1* | 6/2011 | Walker | A61N 1/0464 607/2 |
| 2011/0178586 A1* | 7/2011 | Grey | A61N 1/3787 607/136 |
| 2015/0360030 A1* | 12/2015 | Cartledge | A61N 1/0456 607/136 |
| 2016/0279021 A1 | 9/2016 | Hyde et al. | |
| 2016/0346530 A1* | 12/2016 | Jeffery | A61N 1/0492 |
| 2017/0252562 A1* | 9/2017 | Goldwasser | A61N 1/0456 |
| 2017/0368329 A1* | 12/2017 | Tyler | A61N 1/32 |
| 2018/0264265 A1* | 9/2018 | Black | A61F 7/12 |

FOREIGN PATENT DOCUMENTS

| | | |
|---|---|---|
| CN | 105749420 A | 7/2016 |
| WO | 2017040739 A2 | 3/2017 |

OTHER PUBLICATIONS

EnglishTranslation of CN105749420, Jul. 13, 2016, Li Y et al. (see attached) (Year: 2016).*

* cited by examiner

FUNCTIONAL ELECTRICAL STIMULATION DEVICE FOR REDUCING PREOPERATIVE AND PRENATAL ANXIETY AND METHOD FOR USING SAME

This application is the National Stage Application of PCT/CN2017/116829, filed on Dec. 18, 2017, which claims priority to Chinese Patent Application No.: 201711339695.6, filed on Dec. 14, 2017, which is incorporated by reference for all purposes as if fully set forth herein.

FIELD OF THE INVENTION

The present invention relates to the field of medical technologies, and more particularly to a functional electrical stimulation device for reducing preoperative and prenatal anxiety and a method for using same.

DESCRIPTION OF THE RELATED ART

Preoperative and prenatal (referred to as preoperative for short below) anxiety is a common psychological reaction before surgery, and may cause negative reactions such as palpitation, chest distress, pollakiuria, abdominal pain, and sleep disorder, which affect anesthesia, increase surgical risks, and hamper postoperative recovery of patients. Statistics show that there have been approximately 45,560,000 surgeries in China in 2015. An occurrence rate of preoperative anxiety is approximately 60%, and may be up to 80%. China has witnessed approximately 18,460,000 newborns in 2016, wherein 80% of the gynecological operation patients have suffered from different levels of anxiety. At present, the phenomenon of preoperative anxiety has not drawn enough attention worldwide, and preoperative anxiety is generally treated with medications such as benzodiazepine derivatives, midazolam, and lorazepam throughout the world. Although these medications are effective, they tend to produce toxic and side effects, have relatively high costs, and may result in drug residue after treatment. In addition, psychotherapeutic methods such as psychological counselling and music therapy are also used. However, psychological counselling is impractical in the light of the large population of patients that require surgery. Research demonstrates that functional electrical stimulation has significant effects in pain relief, stimulation of neuromuscular tissues, and regulation of neuroendocrine functions, and the like. Therefore, a safe and side-effect-free electrical stimulation device for reducing preoperative anxiety is provided in the invention.

SUMMARY OF THE INVENTION

To solve the foregoing technical problem, an object of the present invention is to provide a functional electrical stimulation device for reducing preoperative and prenatal anxiety and a method for using same, the device and method can alleviate physiological and psychological symptoms of anxiety of patients.

In one aspect, the invention provides a functional electrical stimulation device for reducing preoperative and prenatal anxiety provided in the present invention comprises a headset, an electrical stimulation patch, an LED display screen, a circuit board, a rechargeable battery, and a wireless terminal, wherein two headphone bodies are symmetrically disposed on the headset, the circuit board and the rechargeable battery are respectively mounted on the two headphone bodies, and a music control button and an electrical stimulation mode and time control button are further mounted on the two headphone bodies, respectively;

two electrical stimulation patches are symmetrically mounted at an interval on a middle portion of the headset, and two LED display screens are respectively mounted on the two electrical stimulation patches;

an audio decoder chip, a button control module, a power switch, an electrical stimulation generation module, a wireless communication module, and a charging port are disposed on the circuit board. The music control buttons, the electrical stimulation mode and time control button, and the LED display screen are all in communication with the circuit board, and the rechargeable battery and the electrical stimulation patches are both electrically connected to the circuit board.

The wireless terminal is independently disposed, and the wireless terminal is in wireless communication with the circuit board.

Preferably, the two headphone bodies are a left headphone body and a right headphone body, the music control button is mounted on an outer wall of the left headphone body, the rechargeable battery is located between the music control button and the left headphone body, the electrical stimulation mode and time control button is mounted on outer wall of the right headphone body, and the circuit board is located between the electrical stimulation mode and time control button and the right headphone body.

Preferably, the music control button comprises a volume button, a song skip button, a music pause and play button, the music control button further comprises a voice input button, and a voice control module is further disposed on the circuit board.

Preferably, the electrical stimulation mode and time control button comprises a switch button, a mode selection button, and a timing button.

Preferably, the charging port is a USB charging port, the wireless communications module is a Wi-Fi module, the rechargeable battery is a lithium battery, and the rechargeable battery is charged via the charging port.

Preferably, a functional electrical stimulation voltage generated by the electrical stimulation generation module is between negative 100 v and positive 100 v, the electrical stimulation generation module comprises a PWM generator, a PWM waveform generated by the PWM generator is between 1 Hz and 1000 Hz, a PWM signal current is between 1 mA and 10 mA, and a duty cycle, a frequency, and an interval of an output waveform is controlled to control frequency and intensity of output electrical stimulation.

Preferably, the wireless terminal is a PAD (Portable Android Device), a mobile phone or a notebook computer.

In another aspect, the invention also provides a method for using a functional electrical stimulation device for reducing preoperative and prenatal anxiety, which comprises the following steps:

S1. after a patient is checked in, checking, by using a management system at a nurse station, whether there is information of the patient, and if yes, directly performing S2, or if no, creating information of the patient and then performing S2;

S2. checking currently available devices on the management system, choosing one electrical stimulation device, and performing S3, wherein each electrical stimulation device is controlled by one corresponding wireless terminal;

S3. inputting the ID number of the patient on the wireless terminal, choosing a sequence number of the electrical stimulation device to perform pairing, entering an interface for selecting music, an electrical stimulation mode, and an electrical stimulation time after the pairing succeeds, wherein feature matching is performed by using intensity and a mode of functional electrical stimulation that are selected by the patient with amplitude and rhythm of music in a headset corresponding to the patient to implement appropriate matching between music and functional electrical stimulation, wherein the intensity and mode of functional electrical stimulation may be adjusted by a doctor according to the patient's condition or may be adjusted by the patient or may be determined by the amplitude and rhythm of the music in the headset, clicking "start" after the intensity and mode are selected, so that the wireless terminal transfers data to the electrical stimulation device, and transfers data such as the information of the patient, the sequence number of the electrical stimulation device, the music, the mode, and time to the management system of the nurse station by using a wireless local area network, and performing S4;

S4. after the device receives a stimulation mode instruction via the wireless network, controlling, by using an audio decoder chip, output of corresponding music, and performing a corresponding anxiety reduction operation according to selected stimulation; and adding, by the management system, a new record to a record of use after receiving the data, changing the status of the electrical stimulation device to "in use", and performing S5;

S5. after the stimulation ends, prompting the patient with voice, wherein the power of a headset device may be manually turned off by the patient or may be automatically turned off by the wireless terminal according to a set time, and the wireless terminal enters a review interface after the headset is turned off, and performing S6; and S6. after a review is given, sending, by the wireless terminal, an end signal and a result of the review to the management system, adding the review to the record, and changing the status of the device to "available" by the management system.

By means of the foregoing technical solutions, the present invention has the following advantages: The functional electrical stimulation device for reducing preoperative and prenatal anxiety can alleviate physiological and psychological symptoms of anxiety of patients by combining functional electrical stimulation and music, thereby improving the effect of treating anxiety disorder. Furthermore, operations are simple and convenient.

These and other objects and advantages of the present invention will become readily apparent to those skilled in the art upon reading the following detailed description by referring to the accompanying drawings.

DETAILED DESCRIPTION OF THE PREFERRED EMBODIMENTS

Figure 1:
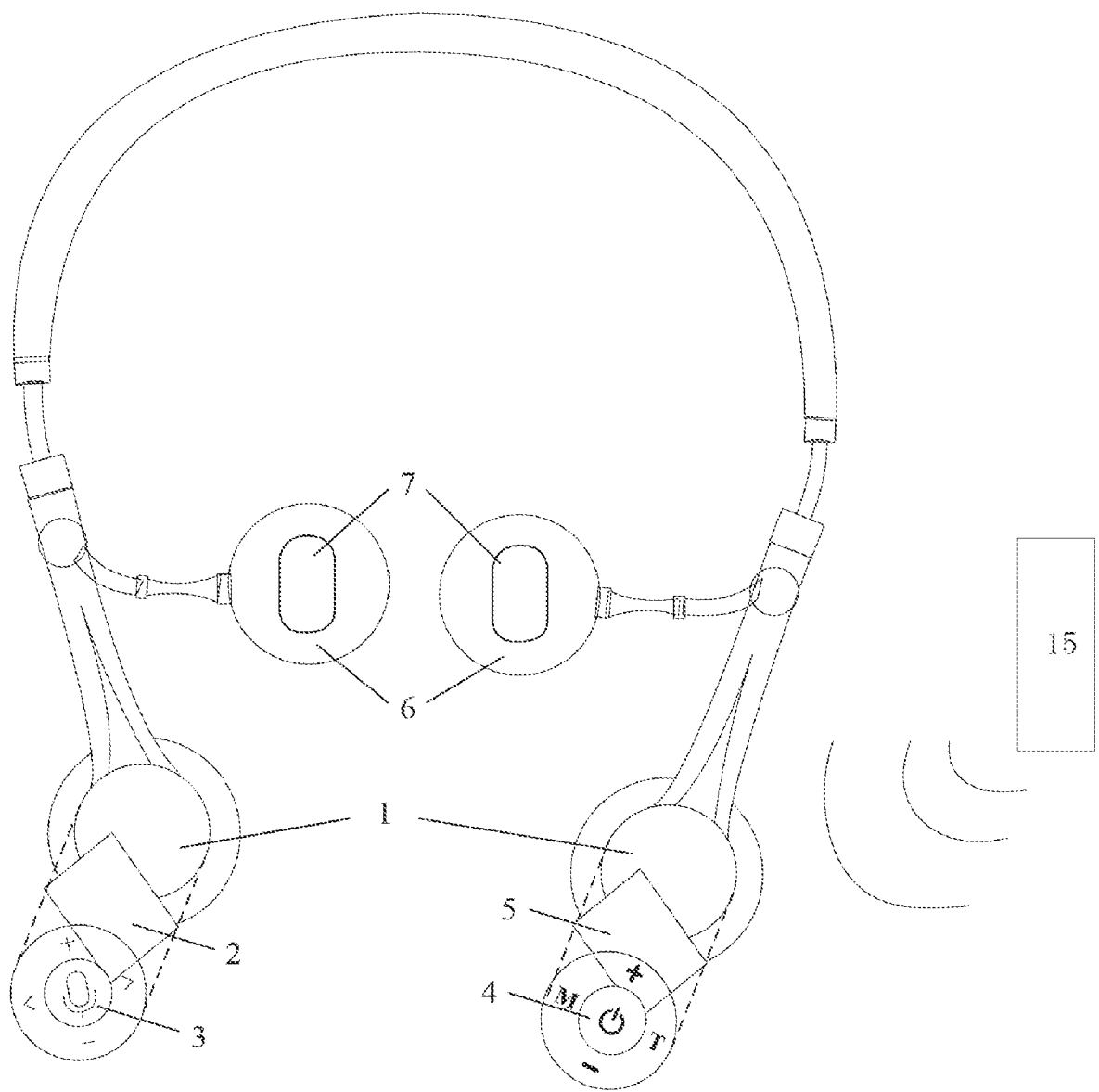
FIG. 1 is an exploded view of a functional electrical stimulation device for reducing preoperative and prenatal anxiety according to the present invention.
Figure 2:
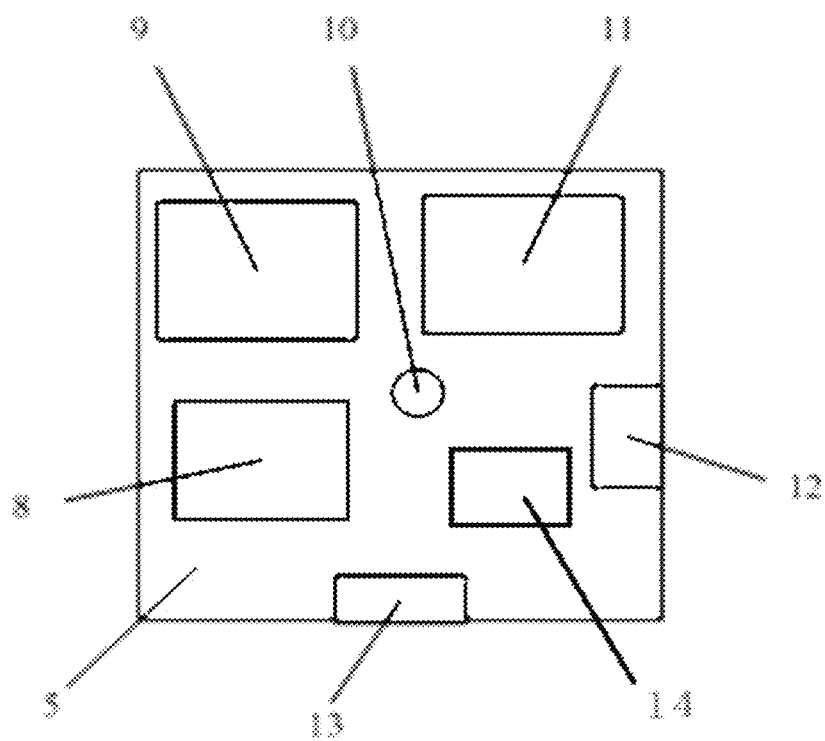
FIG. 2 is a schematic view of a circuit board according to the present invention, wherein: 1—headphone body, 2—rechargeable battery, 3—music control button, 4—electrical stimulation mode and time control button, 5—circuit board, 6—electrical stimulation patch, 7—LED display screen, 8—audio decoder chip, 9—button control module, 10—power switch, 11—electrical stimulation generation module, 12—wireless communications module, 13—charging port; 14—voice control module; and 15—wireless terminal.

The invention will be further illustrated in more detail with reference to the accompanying drawings and embodiments. It is noted that, the following embodiments are only intended for purposes of illustration, but are not intended to limit the scope of the present invention.

Embodiment

A functional electrical stimulation device for reducing preoperative and prenatal anxiety comprises a headset, an electrical stimulation patch 6, an LED display screen 7, a circuit board 5, a rechargeable battery 2, and a wireless terminal 15.

Two headphone bodies 1 are symmetrically disposed on the headset, the circuit board 5 and the rechargeable battery 2 are respectively mounted on the two headphone bodies 1, and a music control button 3 and an electrical stimulation mode and time control button 4 are further mounted on the two headphone bodies 1, respectively.

Two electrical stimulation patches 6 are symmetrically mounted at an interval on a middle portion of the headset, and two LED display screens 7 are respectively mounted on the two electrical stimulation patches 6.

An audio decoder chip 8, a button control module 9, a power switch 10, an electrical stimulation generation module 11, a wireless communications module 12, and a charging port 13 are disposed on the circuit board 5. The music control buttons 3, the electrical stimulation mode and time control buttons 4, and the LED display screen 7 are all in communication with the circuit board 5, and the rechargeable battery 2 and the electrical stimulation patches 6 are both electrically connected to the circuit board 5. The LED display screen 7 is used to display information such as a sequence number, a mode, a remaining time of a current device.

The wireless terminal 15 is independently disposed, and the wireless terminal 15 is in wireless communication with the circuit board 5.

The two headphone bodies 1 are a left headphone body and a right headphone body, the music control button 3 is mounted on an outer wall of the left headphone body, the rechargeable battery 2 is located between the music control button 3 and the left headphone body, the electrical stimulation mode and time control buttons 4 are mounted on outer wall of the right headphone body, and the circuit board 5 is located between the electrical stimulation mode and time control button 4 and the right headphone body. For a mounting manner, the left headphone body and the right headphone body are interchangeable.

The music control button 3 comprises a volume button, a song skip button, a music pause and play button, the music control button 3 further comprise a voice input button, and a voice control module 14 is further disposed on the circuit board 5. Amplitude and rhythm of music may further be controlled by a voice input.

The electrical stimulation mode and time control button 4 comprises a switch button, a mode selection button, and a timing button.

The charging port 13 is a USB charging port, the wireless communication module 12 is a Wi-Fi module, the rechargeable battery 2 is a lithium battery, and the rechargeable battery 2 is charged via the charging port 13. Certainly, the rechargeable battery 2 is not only limited to a lithium battery, and may further be rechargeable batteries such as a nickelcadmium battery. The wireless communications module 12 is not only limited to a Wi-Fi module, and may further be other short-range wireless communication modules such as a Bluetooth module.

A functional electrical stimulation voltage generated by the electrical stimulation generation module 11 is between negative 100 v and positive 100 v, the electrical stimulation generation module 11 comprises a PWM generator, a PWM waveform generated by the PWM generator is between 1 Hz and 1000 Hz, a PWM signal current is between 1 mA and 10 mA, and a duty cycle, a frequency, and an interval of an output waveform is controlled to control frequency and intensity of output electrical stimulation.

A PWM signal generated by the device utilizes an H-bridge circuit and a filter circuit to form a bipolar sine wave or a square wave to produce a stimulation effect. Moreover, a current-limiting circuit is added to the H-bridge circuit to prevent the excessive current from adversely affecting the human body. In addition, some integrating circuits may be used to form an approximate triangle wave. Eventually, different types of stimulation modes having different amplitude and intensity may be formed according to different combinations of waveforms and switching between presence and absence of waveforms to treat the human body.

The wireless terminal 15 is a PAD, a mobile phone or a notebook computer.

A method for using a functional electrical stimulation device for reducing preoperative and prenatal anxiety comprises the following steps:

S1. after a patient is checked in, checking, by using a management system at a nurse station, whether there is information of the patient, and if yes, directly performing S2, or if no, creating information of the patient and then performing S2;

S2. checking currently available devices on the management system, choosing one electrical stimulation device and performing S3, wherein each electrical stimulation device is controlled by one corresponding wireless terminal;

S3. inputting the ID number of the patient on the wireless terminal, choosing a sequence number of the electrical stimulation device to perform pairing, entering an interface for selecting music, an electrical stimulation mode, and an electrical stimulation time after the pairing succeeds, clicking "start" after the intensity and mode are selected, so that the wireless terminal transfers data to the electrical stimulation device, and transfers data such as the information of the patient, the sequence number of the electrical stimulation device, the music, the mode, and time to the management system of the nurse station by using a wireless local area network, and performing S4;

S4. after the device receives a stimulation mode instruction via the wireless network, controlling output of corresponding music by using an audio decoder chip 8, and performing a corresponding anxiety reduction operation according to selected stimulation; and adding a new record to a record of use, by the management system after receiving the data, changing the status of the electrical stimulation device to "in use", and performing S5;

S5. after the stimulation ends, prompting the patient with voice, wherein the power of a headset device may be manually turned off by the patient or may be automatically turned off by the wireless terminal according to a set time, and the wireless terminal 15 enters a review interface after the headset is turned off, and performing S6; and S6. after a review is given, sending an end signal and a result of the review by the wireless terminal 15 to the management system, adding the review to the record, and changing the status of the device to "available" by the management system.

The functional electrical stimulation device for reducing preoperative and prenatal anxiety combines functional electrical stimulation and music to alleviate physiological and psychological symptoms of anxiety of patients. Feature matching is performed by using intensity and a mode of functional electrical stimulation that are selected by the patient and amplitude and rhythm of music in a headset corresponding to the patient to implement appropriate matching between music and functional electrical stimulation, wherein the intensity and mode of functional electrical stimulation may be adjusted by a doctor according to the patient's condition or may be adjusted by the patient or may be determined by the amplitude and rhythm of the music in the headset, so that the effect of treating anxiety disorder is improved, and operations are simplified and facilitated.

The electrical stimulation device is a structure formed by three layers, wherein an outermost layer is a button layer, an intermediate layer is a circuit layer, and an innermost layer is an output layer. The three layers are connected through flexible wire materials. The patient can use the wireless terminal 15 to adjust the music, mode, time, and may also directly adjust on the electrical stimulation device or indirectly adjust by using a voice. The use status of the electrical stimulation device and operations of the patient can be monitored in real time by establishing a link between the wireless terminal 15 and a remote computer terminal, and related data may be transmitted to a management system of the computer terminal for big data analysis or paid use.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A functional electrical stimulation device for reducing preoperative and prenatal anxiety, comprising:
   a headset, two electrical stimulation patches, an LED (Light-Emitting Diode) display screen, a circuit board, a rechargeable battery, and a wireless terminal;
   wherein two headphone bodies are symmetrically disposed on the headset;
   wherein the circuit board and the rechargeable battery are respectively mounted on the two headphone bodies;
   wherein a music control button and an electrical stimulation mode and time control button are further mounted on the two headphone bodies, respectively;
   wherein the two electrical stimulation patches are symmetrically mounted at an interval on a middle portion of the headset, and two LED display screens are respectively mounted on the two electrical stimulation patches;
   wherein an audio decoder chip, a button control module, a power switch, an electrical stimulation generation module, a wireless communication module, and a charging port are disposed on the circuit board;
   wherein the music control button, the electrical stimulation mode and time control button, and the LED display screen are all in communication with the circuit board, and the rechargeable battery;
   wherein the two electrical stimulation patches are both electrically connected to the circuit board;

wherein the wireless terminal is independently disposed, and the wireless terminal is in wireless communication with the circuit board;

wherein the two headphone bodies are a left headphone body and a right headphone body, the music control button is mounted on an outer wall of the left headphone body, the rechargeable battery is located between the music control button and the left headphone body, the electrical stimulation mode and time control button is mounted on outer wall of the right headphone body, and the circuit board is located between the electrical stimulation mode and time control button and the right headphone body;

wherein the music control button comprises a volume button, a song skip button, a music pause and play button, the music control button further comprises a voice input button, and a voice control module is further disposed on the circuit board;

wherein the electrical stimulation mode and time control button comprises a switch button, a mode selection button, and a timing button;

wherein the charging port is a USB charging port, the wireless communication module is a Wi-Fi module, the rechargeable battery is a lithium battery, and the rechargeable battery is charged via the charging port; and wherein a functional electrical stimulation voltage generated by the electrical stimulation generation module is between negative 100 v and positive 100 v, the electrical stimulation generation module comprises a PWM generator, a PWM waveform generated by the PWM generator is between 1 Hz and 1000 Hz, a PWM signal current is between 1 mA and 10 mA, and a frequency and an intensity of an output electrical stimulation are controlled by controlling a duty cycle, a frequency, and an interval of an output waveform.

2. The functional electrical stimulation device for reducing preoperative and prenatal anxiety according to claim 1, wherein the wireless terminal is a PAD (Portable Android Device), a mobile phone or a notebook computer.

3. A method for using a functional electrical stimulation device for reducing preoperative and prenatal anxiety, including steps S1 through S6, the steps comprising:

S1, after a patient is checked in, checking whether there is information of the patient using a management system at a nurse station, and if yes, directly performing S2, or if no, creating information of the patient and then performing S2;

S2, checking currently available devices on the management system, choosing one electrical stimulation device and performing S3, wherein each electrical stimulation device is controlled by one corresponding wireless terminal;

S3, inputting the identification (ID) number of the patient on the wireless terminal, choosing a sequence number of the electrical stimulation device to perform pairing, entering an interface for selecting music, an electrical stimulation mode and an electrical stimulation time after the pairing succeeds, wherein feature matching is performed by using an intensity and a mode of functional electrical stimulation that are selected by the patient with an amplitude and a rhythm of music in a headset corresponding to the patient to implement appropriate matching between the music and the functional electrical stimulation, the intensity and the mode of the functional electrical stimulation being adjusted by one of the patient or a doctor according to the patient's condition, or determined by the amplitude and the rhythm of the music in the headset, after the intensity and the mode are selected, enabling the wireless terminal to transfer a first data to the electrical stimulation device, and transfer of a second data including the information of the patient, the sequence number of the electrical stimulation device, the music, the mode, and the electrical stimulation time to the management system of the nurse station by using a wireless local area network, and performing S4;

S4, after the device receives a stimulation mode instruction via the wireless network, controlling output of the corresponding music by using an audio decoder chip, and performing a corresponding anxiety reduction operation according to the selected stimulation; and adding a new record to a record of use by the management system after receiving the second data, changing the status of the electrical stimulation device to in-use state, and performing S5;

S5, after the stimulation ends, prompting the patient with voice, wherein the power of the headset is turned off by at least one of manually by the patient or automatically by the wireless terminal according to a set time, and the wireless terminal enters a review interface after the headset is turned off, and performing S6; and S6, after a review is given, sending an end signal and a result of the review by the wireless terminal to the management system, adding the review to the record, and changing the status of the device to available state by the management system.

\* \* \* \* \*